（12） United States Patent
Baker (10) Patent No.: US 8,152,027 B1
(45) Date of Patent: Apr. 10, 2012

(54) SANITIZING BARRIER OPENING DEVICE (76) Inventor: Ronald G. Baker, Fayetteville, AR (US)

( * ) Notice: Subject to any disclaimer, the term of this patent is extended or adjusted under 35 U.S.C. 154(b) by 405 days.

(21) Appl. No.: 12/387,531

(22) Filed: May 4, 2009

(51) Int. Cl.
*B67D 1/07* (2006.01)

(52) U.S. Cl. .. 222/192; 222/1; 222/153.01; 222/153.04; 222/321.8; 222/505

(58) Field of Classification Search .................. 222/180, 222/505, 509, 153.01, 153.03, 153.04, 153.14, 222/192, 1
See application file for complete search history.

(56) References Cited

U.S. PATENT DOCUMENTS

| | | | |
|---|---|---|---|
| 2,044,904 A | 6/1936 | Heisig | 292/347 |
| 3,273,756 A | 9/1966 | Levy et al. | 222/180 |
| 3,390,817 A | 7/1968 | Heropoulos | 222/180 |
| 3,608,784 A * | 9/1971 | Brown et al. | 222/180 |
| 3,877,005 A * | 4/1975 | Apgar | 340/304 |
| 3,967,478 A | 7/1976 | Guinn | 70/144 |
| 4,090,644 A * | 5/1978 | Fegley | 222/180 |
| 4,202,471 A * | 5/1980 | Fegley | 222/153.11 |
| 4,896,144 A * | 1/1990 | Bogstad | 340/691.6 |
| 5,808,553 A | 9/1998 | Cunningham | 340/573 |
| 6,029,600 A | 2/2000 | Davis | 116/200 |
| 7,320,418 B2 | 1/2008 | Sassoon | 222/649 |
| 7,458,742 B2 | 12/2008 | Stropkay et al. | 401/205 |
| 8,061,565 B1 * | 11/2011 | Baker | 222/192 |

* cited by examiner

*Primary Examiner* — Frederick C. Nicolas
(74) *Attorney, Agent, or Firm* — Keisling & Pieper, PLC; Stephen D. Schrantz (57) ABSTRACT

The present invention provides a method and device for sanitizing a user's hands prior to the user being granted access to an area. A barrier restricts access to a particular area without sanitization of the user's hands. A locking finger of the present invention prevents opening of the barrier. The locking finger adjusts between an allow access position and a prevent access position to prevent a user from passing the barrier without adjusting the locking finger to the allow access position. To open the barrier, a user must adjust an access arm from a lock position to an unlock position to adjust the position of the locking finger. The user pivots the access arm towards the barrier if the barrier is opened by pushing the barrier. The user pivots the access arm away from a barrier that requires to be pulled upon. The pivoting of the access arm releases a cleaning substance to the user's hands pivoting the access arm requiring the user to sanitize his hands before accessing the area beyond the barrier.

20 Claims, 6 Drawing Sheets

FIG. 20

SANITIZING BARRIER OPENING DEVICE

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

I. Field of the Invention

The present invention relates to maintaining a sterile and sanitized environment by enforcing personal sanitization and hygiene. More particularly, the present invention relates to sanitization in public settings including but not limited to healthcare settings, restaurants, public restrooms, and other locations where disease and germs may be spread. The cost of fighting hospital acquired infections is estimated to be at least $30 billion per year. The drug-resistant forms of these infections, such as MRSA, can cost $30,000 per case to combat. Sadly, these infections kill more than 90,000 Americans every year. MRSA kills around 18,000 people every year. Most of these infections are transferred from patient to patient on surfaces that are not sanitized, particularly on the hands of people such as staff and visitors.

The present invention provides a simple method that mechanically ensures that a person sanitizes his/her hands. Unclean hands assist in the spread of infections. Thus, unclean hands cost patients, hospitals and insurance companies a large sum of money combating such infections. The present invention ensures sterilization of the user's hands and prevents the introduction and spread of infections from a user's hands. The present invention also creates an economic benefit by reducing the costs associated with combating such infections.

Restaurants and healthcare settings such as hospitals have hygiene requirements that require their staff and employees to clean their hands. Often, restaurants and hospitals rely on an honor type system to remind the employees and staff to wash their hands. Signs also remind users to clean their hands. Even with the mandatory requirements and signs, users continue to improperly wash their hands. Furthermore, many users only rinse their hands with water that does not properly sanitize the user's hands.

II. Description of the Known Art

Patents and patent applications disclosing information relevant to hygienic systems are disclosed below. These patents and patent applications are hereby expressly incorporated by reference in their entirety.

U.S. Pat. No. 7,458,742 issued to Stropkay on Dec. 2, 2008 ("the '742 patent") teaches a door handle and liquid dispensing apparatus including a housing configured to attach to an associated door and a porous material. The housing taught by the '742 patent at least partially defines a reservoir configured to hold a liquid for cleaning a person's hand when the person opens the associated door. The porous material is disposed in and extends from the reservoir. A portion of the porous material is disposed adjacent a location typically touched by the person's hand when opening the associate door.

The invention taught by the '742 patent is configured to provide hand sanitizing and/or hand cleaning liquid, which includes lotion, to a person whether the person pushes against the assembly 10 to open the door or pulls the assembly 10 to open the door. The assembly 10 taught by the '742 patent is described as a "door handle" assembly; however, the term "door handle" or "handle" is not limited to simply a bar that is grasped and pulled to open the door to which the bar is attached. The term "door handle" or "handle" as used in the '742 patent refers to a portion of the assembly that is typically touched by the person's hand when opening the door, whether it be by pushing or pulling the door.

U.S. Pat. No. 2,044,904 issued to Heisig on Jun. 23, 1936 ("the '904 patent") teaches a means for automatically supplying to the hands of the user a restricted and minute amount of a liquid antiseptic as an instant of the user rotating the knob. The '904 patent teaches two liquid containing compartments filled with a watery solution of a suitable antiseptic, preferably by the use of a pressure syringe into discharge vents which in this case function as filling vents and the liquid as intruded raised in the compartment. The '904 patent teaches when a user passes his fingers across the outer face of the vent incidental to rotating the knob the operator withdraws through the vent, apparently by a frictional or perhaps by an adhesion action, a minute quantity of the antiseptic solution.

U.S. Pat. No. 6,029,600 issued to Davis on Feb. 29, 2000 ("the '600 patent") teaches a device for assuring that restroom users are effectively reminded to wash and cleanse their hands. The '600 patent teaches a spray pump attached adjacent to an exterior door-handle to a restroom and is activated either by the turning of the handle or by the opening of the door. The spray pump taught by the '600 patent includes a spray nozzle which sprays the user's front palm and/or back of the hand with a dye stain when the door-handle is opened. The '600 patent teaches that the dye stain is non-toxic fast drying and easily washable with cleanser such as soap and water. The dye stain taught by the '600 patent can be visible in natural light and include colors such as red, yellow, blue and the like. Alternatively, the dye stain taught by the '600 patent can be only visible to infrared light. The device taught by the '600 patent can be used with round circular door-handles and lever door-handles. The '600 patent teaches that a shield around the door handle can discourage attempts to defeat the staining.

U.S. Pat. No. 4,896,144 issued to Bogstad on Jan. 23, 1990 ("the '144 patent") teaches a warning system adapted to warn someone to wash their hands prior to leaving or entering a facility in which hand washing is important. The '144 patent teaches a system that includes a door activated system that can be either visible or audible or both and can include a door locking system and a remote signalling system. The warning system taught by the '144 patent is armed when the door is opened to permit entry into the facility and is de-activated upon the acutation of hand-washing facilities. In one embodiment, the system taught by the '144 patent is used in a bathroom and the warning system can be activated by the flushing of a toilet.

The '144 patent also teaches that the consequences of not washing one's hands after using the bathroom are so dire as to require extreme measures to ensure that hands are always washed after using the bathroom. In such extreme situations, the '144 patent teaches that the door 12 can be locked after entry and only unlocked after the hand washing facilities have been used. The control unit 36 and the ingress and egress signaling systems taught by the '144 patent can be used to carry out this function. For this, the system 10 taught by the '144 patent includes a door locking element 80 on the door frame and connected to the control unit 36 via a line connector 82 and adapted to co-operate with a locking mechanism 84 on the door to prevent opening of the door unless the hand washing facilities have been activated. The '144 patent teaches that upon activating a hand-washing facility, a signal can be sent to the control unit 36 to unlock the door via the just-described door locking system.

U.S. Pat. No. 3,967,478 issued to Guinn on Jul. 6, 1976 ("the '478 patent") teaches an apparatus for unlatching a door to a hygienic area actuated by sensor electrodes in contact with the electrolytic residue of a cleansing agent upon the hand or limb of a person desiring access to the hygienic area. The '478 patent teaches that the personnel desiring entry must have washed or cleansed his hands or arms or other limbs with the required germicidal cleansing agent, such as soap, which will normally leave a sufficient electrolytic residue on his hand to establish a current between the electrodes when the hand is placed in contact with both electrodes. The '478 patent teaches that the current established through the electrolytic residue and the electrodes will then actuate the switch device to close the circuit through the coil of the electromagnetic bolt mechanism for unlatching the door, thereby permitting entry to the hygienic area.

U.S. Pat. No. 3,390,817 issued to Heropoulus on Jul. 2, 1968 ("the '817 patent") teaches a holder body having inlet and outlet passages, means for detachably securing an aerosol container in communication with the inlet passage and means for securing fluid dispersing means to the outlet passage and actuator means in the body for engaging and opening the aerosol valve when a door is opened.

U.S. Pat. No. 3,273,756 issued to Levy et al. on Sep. 20, 1966 ("the '756 patent") teaches a device for the automatic treatment of the air in a room and, more particularly to a device for the automatic spraying of the air in a room, as with a sterilizing, de-odorizing or perfuming spray. The '756 patent teaches that when the frame containing a dispenser is in place and the door is opened, the top edge of the door will engage the projecting resilient strip and will move and offset it and the bar extension outwardly and upwardly to clear the door top without any difficulty and without any effect on the pressure dispenser. However, when the door is closed, its edge will engage against the outer face of the strip projection and press it inwardly towards the frame, causing the strip and the bar extension to which it is attached to be pushed towards the supporting frame and thereby lowering the bar section and its extension onto the nozzle head, to depress the same, causing a discharge of spray through the valve of the pressure dispenser that is opened by such nozzle head movement.

U.S. Pat. No. 5,808,553 issued to Cunningham on Sep. 15, 1998 ("the '553 patent") teaches an apparatus for unlocking the door to a hygienic area formed by a circuit having a pair of series connected, normally open push button switches disposed in spaced apart relation at lateral limits of a lavatory. The '553 patent teaches that when the switch buttons are simultaneously depressed for a predetermined time, as by the little finger of each hand of a worker, soap sprays from overhead spray heads on the worker's hands, and after the predetermined time delay, unlocks the door.

The '553 patent teaches that upon the entry, the door automatically locks behind the worker and will not open until a certain sequence of steps are performed by the worker using the facilities. The '553 patent teaches that the worker, using both little fingers of his hands, pushes dual buttons on opposite sides of a lavatory simultaneously which sprays a quantity of disinfectant soap on his hands and closes a circuit and unlocking the door.

U.S. Pat. No. 7,320,418 issued to Sassoon on Jan. 22, 2008 ("the '418 patent") teaches controlled sanitizing by dispensing a germicide, such as a disinfectant, antibacterial solution or cleansing agent at intervals. The system taught by the '418 patent can include a housing sized to seat an aerosol can and a control circuit that operates to momentarily open a valve on the aerosol can through action of a gear system upon an aerosol delivery tube. The '418 patent teaches a sensor that responds to displacement of the delivery tube to deliver state signals to the control circuit. The control circuit taught by the '418 patent prevents action of the gear system in the event that the state signals fail at least one prescribed condition. The '418 patent also teaches a method that registers at least the displacement of the delivery tube via the sensor and prevents subsequent displacements and hence subsequent sanitizing in the event that the sensor has not registered at least the displacement of the delivery tube. The method taught by the '418 patent ensures that a suitable aerosol can has been properly loaded in the dispenser. The '418 patent also teaches that the motor actuation cycle can be suppressed if certain external conditions are detected such as the presence of a hand of a person in the vicinity of the sanitizer unit 200.

Therefore, the present invention is needed to improve sanitization, hygiene, and cleanliness. The present invention is also needed to sterilize the user's hands to maintain a clean environment. The present invention is also needed to require a person to clean his hands before passing through a barrier to access a particular area.

SUMMARY OF THE INVENTION

The present invention provides a method and device for sanitizing a user's hands prior to the user being granted access to an area. The present invention utilizes a cleaning substance including but not limited to disinfecting solutions, disinfectants, antibacterial solutions, germicidal solutions, hand cleaners, hand cleaner preparations, skin cleanser, soap, antimicrobial and antibacterial lotion soap, instant hand sanitizers, instant hand disinfectants, and other known cleansers. The present invention prevents the opening of a barrier including but not limited to a door, gateway, gate, a passageway, as well as to other doors leading to other locations where it might be desirable to require cleaning of a user's hands prior to entering the area. The present invention may be utilized in areas that require sterile conditions or in areas in which cleanliness is needed or recommended such as hospitals, kitchens, restrooms, etc.

The present invention utilizes a barrier that prevents people from accessing certain areas. The barrier promotes sterile conditions within areas by restricting access to areas to only those people who have cleaned their hands. The present invention requires cleaning of the hands prior to granting access to the areas by preventing the barrier from opening until an amount of cleaning substance is applied to the user's hands. A locking finger of the present invention prevents opening of the barrier. The locking finger adjusts between an allow access position and a prevent access position. The locking finger in the allow access position allows a user to open the barrier. The locking finger in the prevent access position prevents the barrier from opening when the barrier is in the closed position. In one embodiment of the present invention, the locking finger is biased to the prevent access position.

The present invention also provides an access arm that adjusts between a lock position and an unlock position. In one embodiment of the present invention, the access arm is biased to a lock position. The access arm has two ends, a free end and an attached end. The free end of the access arm pivots in relation to the attached end of the access arm to adjust the access arm between the lock position and the unlock position. Pivoting of the access arm adjusts the position of the locking finger. Adjustment of the access arm to the lock position places the locking finger in a prevent access position. Adjustment of the access arm to the unlock position places the locking finger in an allow access position.

The present invention also provides a container that stores a cleaning substance. The container has a dispensing aperture from which the cleaning substance is released from the container. The container may also include a nozzle extending from the container with the dispensing aperture. The present invention releases the cleaning substance from the dispensing aperture when the access arm is pivoted to the unlock position. The dispensing aperture releases the cleaning substance such that the cleaning substance contacts the user's hands pivoting the access arm. By releasing the cleaning substance when the access arm is pivoted to the unlock position, the present invention releases the cleaning substance onto a user's hands while a user attempts to access the area being restricted by the barrier.

The present invention also teaches a method for mechanically preventing access to an area that requires a user to pass a barrier prior to entering an area. The present invention restricts access to the area to only those who have passed the barrier. A locking finger of the present invention in the prevent access position prevents the barrier from adjusting to an open position that allows users to pass through the barrier. The present invention requires a user to pivot a free end of an access arm to adjust the access arm from a lock position to an unlock position. The present invention then releases an amount of cleaning substance towards the access arm to contact the hands of the user who has pivoted the access arm. The pivoting of the access arm adjusts the locking finger from the prevent access position to the allow access position. The locking finger in the allow access position allows the barrier to move to the open position to allow a user to pass through the barrier.

It is an object of the present invention to provide a device and system to assist in the application of a cleansing substance to a user.

It is a further object of the present invention to maintain cleanliness.

It is a further object of the present invention to prevent access to areas prior to proper cleaning.

It is a further object of the present invention to minimize the spread of infection and disease.

It is a further object of the present invention to ensure compliance with hygiene standards.

These and other objects and advantages of the present invention, along with features of novelty appurtenant thereto, will appear or become apparent by reviewing the following detailed description of the invention.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views.

DETAILED DESCRIPTION

Figure 1:
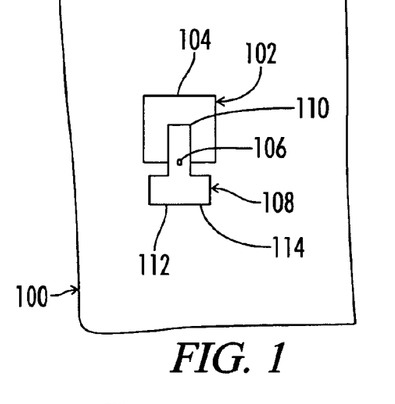
FIG. 1 is an environmental view of one embodiment of the present invention.
Figure 2:
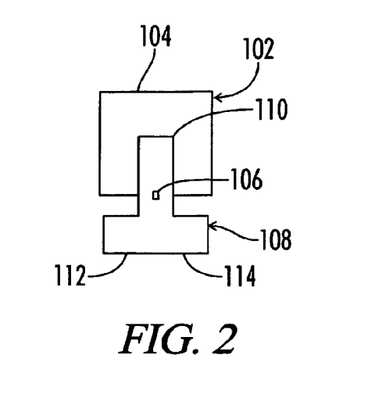
FIG. 2 is a front view thereof.

Referring to FIGS. 1 and 2, the dispenser of one embodiment of the present invention is generally shown as 102. In the embodiment shown in FIG. 1, container 104 mounts to barrier 100. In other embodiments, the container 104 may be mounted elsewhere as long as the container 104 can supply the cleaning substance to a user's hands. Barrier 100 prevents access to the area beyond barrier 100. Barrier 100 restricts access beyond barrier 100 to those who have had the cleaning substance released into their hands. Barriers include but are not limited to a door, gateway, gate, a passageway, as well as to other doors leading to other locations where it might be desirable to require cleaning of a user's hands prior to entering the area.

The present invention utilizes an access arm 108 to grant access beyond the barrier 100. Access arm 108 has two ends, an attachment end 110 and a free end 112. In one embodiment of the present invention, the attachment end 110 of access arm 108 is pivotally attached to container 104. In another embodiment, the attachment end 110 of access arm 108 is pivotally attached to barrier 100. The free end 112 of access arm 108 pivots in relation to attached end 110 of access arm 108. The access arm 108 pivots between a lock position and an unlock position which will be discussed below. As the access arm 108 pivots to the unlock position, dispensing aperture 106 releases an amount of a cleaning substance to be applied to the hands of the user that pivots the access arm 108. In some embodiments of the present invention, the present invention provides contact body 114 for a person to push or pull depending upon the type of barrier 100 to be opened.

Because some barriers 100 are hinged to swing in one direction, the present invention provides different dispensers that assist opening the barrier when the barrier requires to be pushed or whether the barrier requires to be pulled. Different embodiments of the dispenser 102 depicted in FIG. 1 are configured to provide a cleaning substance to a person whether the person pushes or pulls the barrier open. The different embodiments of the present invention release a cleaning substance and adjust the locking finger to the allow access position whether the user pushes against the access arm 108 to open the barrier 100 or pulls the access arm 120 to open the barrier 100.

Figure 3:
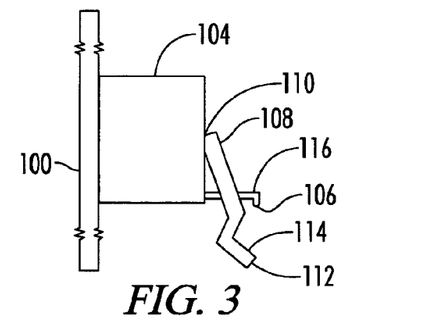
FIG. 3 is a left side view thereof.
Figure 4:
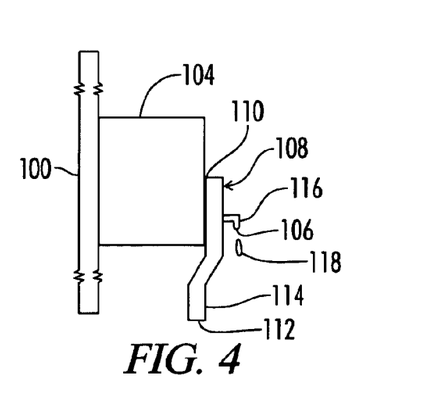
FIG. 4 is another left side view thereof.

FIGS. 3 and 4 show one embodiment of the present invention that opens the barrier 100 when the user pivots access arm 108 towards barrier 100 to the unlock position. FIG. 2 shows access arm 108 in the locked position. Access arm 108 pivots towards barrier 100. With reference to FIG. 2, access arm 108 is pivotally attached at attachment end 110. In one embodiment of the present invention, attachment end 110 of access arm 108 is pivotally attached to container 104. In another embodiment, access arm 108 is pivotally attached to barrier 100. Attachment end 110 of access arm 108 may be attached in other manners. Attachment end 110, 122 of access arm 108, 120 is attached in relation to barrier 100 such that pivoting of the free end 112, 124 of access arm 108, 120 towards or away from barrier 100 assists a user in opening barrier 100. In this embodiment, access arm 108 is biased away from the door to the lock position. Access arm 108 pivots from the lock position in FIG. 3 towards the barrier 100 to the unlock position shown in FIG. 4. As seen in FIGS. 3 and 4, access arm 108 provides contact body 114 to be pushed by a person opening the barrier 100. To open the barrier 100, the user pivots the access arm 108 toward barrier 100 to push barrier 100 open. Pivoting access arm 108 towards the barrier 100 to the unlock position as shown in FIG. 4 releases an amount of cleaning substance 118 from dispensing aperture 106. In one embodiment of the present invention, nozzle 116 extends through access arm 108 to release cleaning substance 118 from dispensing aperture 106. The present invention utilizes known pumps and aerosol containers, as used in known substance dispensers, to release the cleaning substance from the dispensing aperture.

Figure 5:
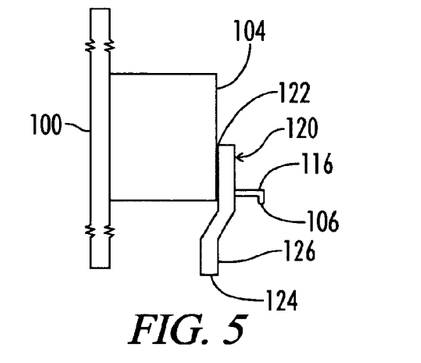
FIG. 5 is a left side view of one embodiment of the present invention.
Figure 6:
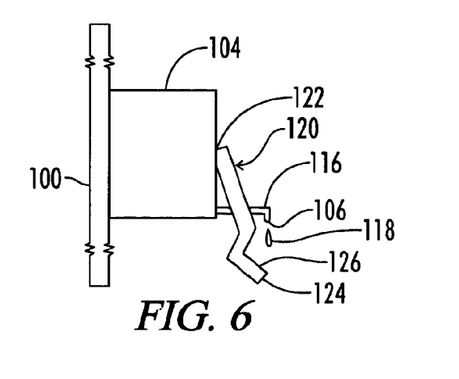
FIG. 6 is another left side view thereof.

FIGS. 5 and 6 show another embodiment of the present invention that requires a user to pivot access arm 120 away from barrier 100 to open the barrier 100. Similar to access arm 108, access arm 120 has two ends, attachment end 122 and free end 124. Access arm 120 functions similarly to access arm 108 in that access arm 120 pivots towards and away from barrier 100. Attachment end 122 of access arm 120 is pivotally attached such that free end 124 of access arm 120 pivots towards and away from the barrier 100 to assist the user in opening barrier 100. In one embodiment, attachment end 122 of access arm 120 is pivotally attached to container 104. In another embodiment, attachment end 122 of access arm is pivotally attached to the barrier 100. Similar to access arm 108, attachment end 122 of access arm 120 may be attached in other manners. Attachment end 122 of access arm is attached in relation to barrier 100 such that pivoting of access arm 120 away from barrier 100 assists a user in opening barrier 100. FIG. 5 shows attachment arm 120 in the lock position. FIG. 6 shows access arm 120 pivoted away from barrier 100 to the unlock position to allow opening of barrier 100. In this embodiment, free end 124 of access arm 120 is biased towards the door to the lock position. As seen in FIGS. 5 and 6, access arm 120 provides contact body 126 to be grasped by a person to pivot free end 124 of access arm 120 away from barrier 100 to open the barrier 100. To open the barrier, the user pivots the access arm 124 away from barrier 100 to pull barrier 100 open.

Figure 7:
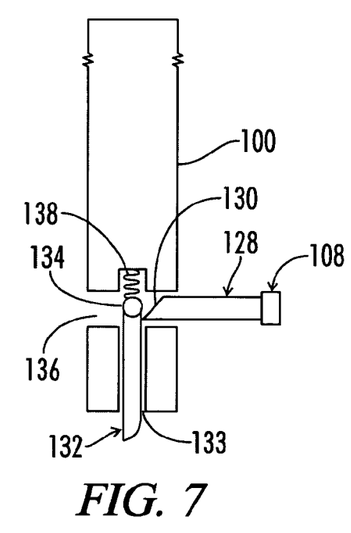
FIG. 7 is a sectional view of one embodiment of the present invention.
Figure 8:
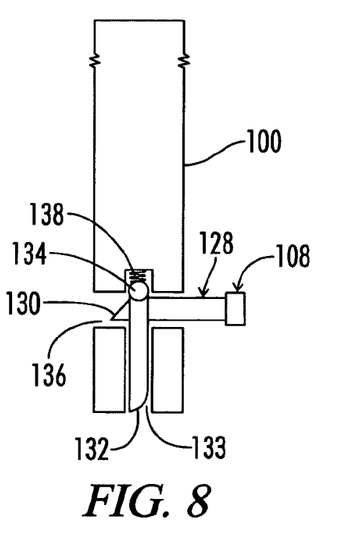
FIG. 8 is another sectional view of one embodiment of the present invention.

FIGS. 7 and 8 show a cutaway view of access arm 108 adjusting the locking finger 132 between the prevent access position to the allow access position. FIG. 7 shows the locking finger 132 in the prevent access position. FIG. 8 shows locking finger 132 in the allow access position. In this embodiment, adjustment arm 128 is attached to access arm 108. As a user pivots access arm 108 towards barrier 100 in a pushing motion, access arm 108 forces adjustment arm 128 through barrier aperture 136 of barrier 100 and adjustment aperture 144 of locking finger 132. Adjustment finger 130 of adjustment arm 128 enters adjustment aperture 144 forcing locking roller 134 to move across adjustment finger 130. The movement of locking roller 134 adjusts locking finger 132 to the allow access position shown in FIG. 8. Continuing to refer to FIG. 7, spring 138 biases the locking finger to the prevent access position shown in FIG. 7. The force applied through adjustment finger 130 causes locking roller 134 to overcome the force of spring 138 to place locking finger 132 into the allow access position shown in FIG. 8.

Figure 9:
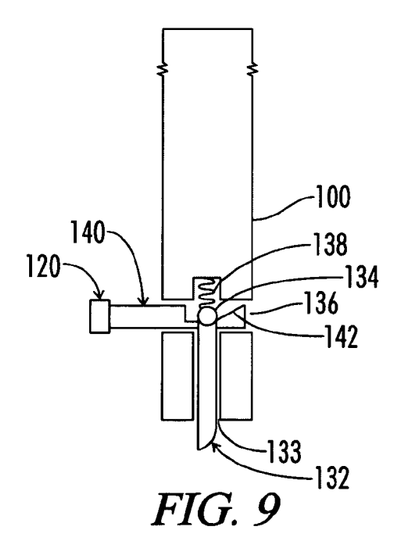
FIG. 9 is a sectional view of one embodiment of the present invention.
Figure 10:
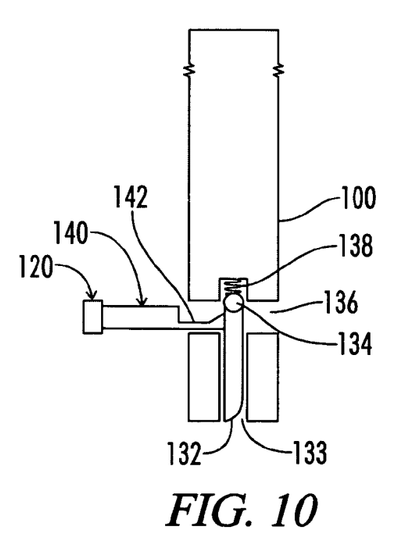
FIG. 10 is another sectional view of one embodiment of the present invention.

FIGS. 9 and 10 show a cutaway view of access arm 108 adjusting the locking finger 132 between the prevent access position to the allow access position. FIG. 9 shows locking finger 132 in the prevent access position. FIG. 10 shows locking finger 132 in the allow access position. In this embodiment, adjustment arm 140 is attached to access arm 120. As a user pivots access arm 120 away from barrier 100 in a pulling motion, access arm 120 forces adjustment arm 140 through barrier aperture 136 of barrier 100 and adjustment aperture 144 of locking finger 132. Unlike access arm 108, access arm 120 pulls adjustment arm 140 through adjustment aperture 144. Adjustment finger 142 of adjustment arm 140 forces locking roller 134 to move across adjustment finger 142 to adjust locking finger 132 to the allow access position shown in FIG. 10. Spring 138 biases the locking finger to the prevent access position shown in FIG. 9. The force applied through adjustment finger 142 causes locking roller 134 to overcome the force of spring 138 to place locking finger 132 into the allow access position shown in FIG. 10.

Referring to FIGS. 7-10, locking finger 132 retracts into locking aperture 133 when the locking finger 132 is adjusted to the allow access position. Locking finger 132 extends from the locking aperture 133 when locking finger 132 is adjusted to the prevent access position. When extending from locking aperture 133, locking finger 132 is adapted to enter a receiving aperture on an adjacent wall, door frame, door jamb, latch, etc. Reception of the locking finger 132 in receiving aperture prevents the barrier from adjusting from the closed position to the open position. To open the barrier, locking finger 132 must be adjusted to the allow access position.

Figure 11:
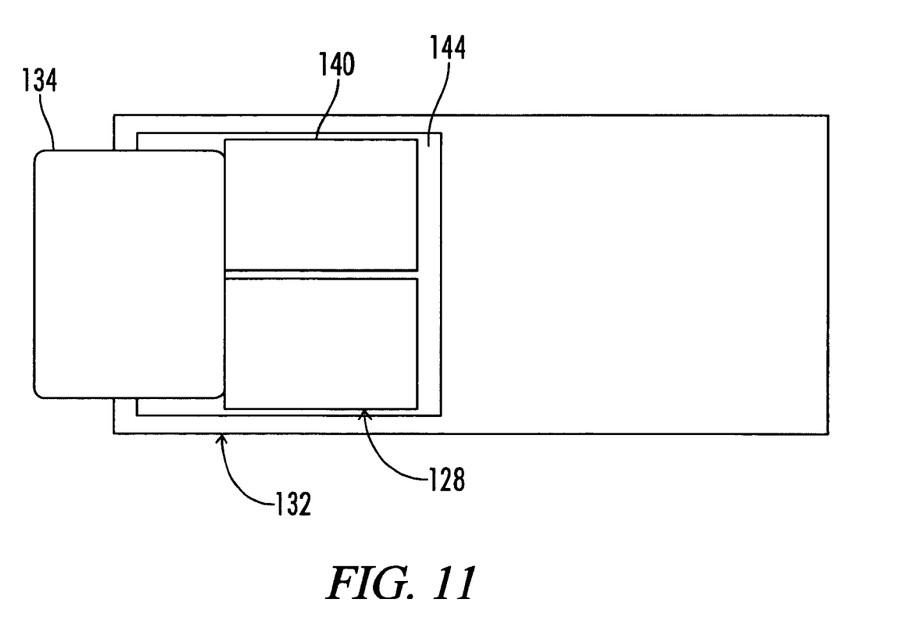
FIG. 11 is a sectional view of one embodiment of the present invention.

Referring to FIG. 11, locking finger 132 provides adjustment aperture 144 for adjustment arm 128, adjustment finger 130, adjustment arm 140, and adjustment finger 142 to pass through locking finger 132 for adjustment of locking finger 132. Adjustment arms 128, 140 have two ends, one end attached to access arm 108, 120, and the other end serving as adjustment finger 130, 142. Adjustment finger 130, 142 retains locking finger 132 within locking aperture 133. Adjustment finger 130, 142 also provides an inclined segment that allows movement of locking roller 134 across adjustment arms 128, 140 and adjustment fingers 130, 142. The movement of locking roller 134 across adjustment fingers 130, 142 forces locking finger 132 to either extend from or retract into locking aperture 133. Locking roller 134 adjusts the position of the locking finger 132 through movement over the inclined section of adjustment finger 130, 142. As adjustment arms 128, 140 move through adjustment aperture 144, locking roller 134 contacts different areas of adjustment arms 128, 140 and adjustment fingers 130, 142. Adjustment arms 128, 140 and adjustment fingers 130, 142 force locking finger 132 to adjust between the prevent access position and the allow access position. Adjustment fingers 130, 142 adjust the position of locking finger 132 within barrier 100 to allow for closing and opening barrier 100 to restrict access. Adjustment fingers 130, 142 operate independently to open barrier 100. Adjustment finger 130 moves independently in relation to adjustment finger 142. Likewise, adjustment finger 142 moves independently in relation to adjustment finger 130. The independence of adjustment fingers 130, 142 allows opening of the barrier without releasing the cleaning substance on both sides of the barrier.

Movement of locking roller 134 across the inclined segment of adjustment fingers 130, 142 force locking finger 132 to retract into locking aperture 133 or extend from locking aperture 133. As shown in FIGS. 7-10, the shape of adjustment fingers 130, 142 vary according to whether access arm is to be pushed as in FIGS. 7 and 8 or pulled as in FIGS. 9-10. The shape of adjustment fingers 130, 142 bias the locking finger 132 between a prevent access position shown in FIGS. 7 and 9 and an allow access position shown in FIGS. 8 and 10 depending upon the movement of adjustment fingers 130, 142. Referring to FIGS. 7 and 8, the free end 112 of access arm 108 pivoted towards the barrier 100 to the unlock position causes adjustment arm 128 and adjustment finger 130 to pass through adjustment aperture 144. Locking roller 134 moves across the inclined section of adjustment finger 130 causing locking finger to retract within locking aperture 133 to the allow access position. One embodiment of the present invention biases the free end 112 of access arm 108 to pivot away from barrier 100 to the lock position. The biasing of access arm 108 away from the barrier causes movement of the locking roller 134 down the inclined section of adjustment finger 130. Movement of locking roller 134 down the inclined section of adjustment finger 130 adjusts locking finger 132 to the prevent access position shown in FIG. 7.

Referring to FIGS. 9 and 10, the free end 124 of access arm 120 pivoted away from barrier 100 to the unlock position causes adjustment arm 140 and adjustment finger 142 to pass through adjustment aperture 144. Locking roller 134 moves across the inclined section of locking finger 142 causing locking finger 132 to retract within locking aperture 133 to the allow access position. One embodiment of the present invention biases the free end 124 of access arm 120 toward barrier 100 to the lock position. The biasing of access arm 120 toward the barrier causes movement of the locking roller 134 down the inclined section of adjustment finger 142. Movement of locking roller 134 down the inclined section of adjustment finger 142 adjusts locking finger 132 to the prevent access position shown in FIG. 10.

Figure 12:
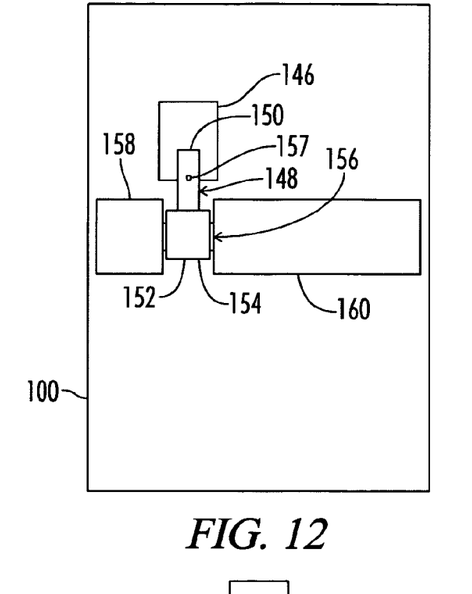
FIG. 12 is an environmental view of one embodiment of the present invention.
Figure 13:
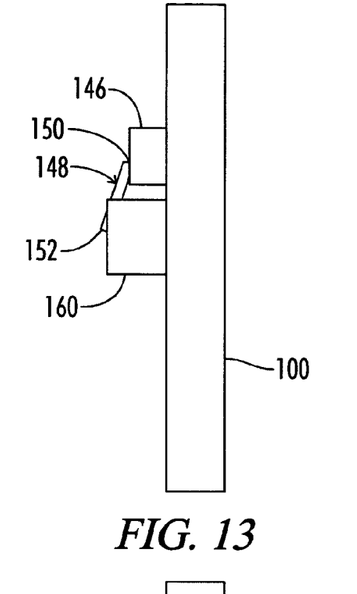
FIG. 13 is an environmental view of one embodiment of the present invention.

FIGS. 12-15 show another embodiment of the present invention that allows existing barriers to be retrofitted with the present invention. FIG. 12 shows a barrier 100 with a push plate 156. To open barrier 100 shown in FIG. 12, the user pushes the push plate 156 towards the barrier 100. As shown in FIGS. 12 and 13, the present invention prevents access beyond barrier 100 by limiting the area of push plate 100 exposed to the user. Guarding bodies 158, 160 prevent access to push plate 156.

Figure 14:
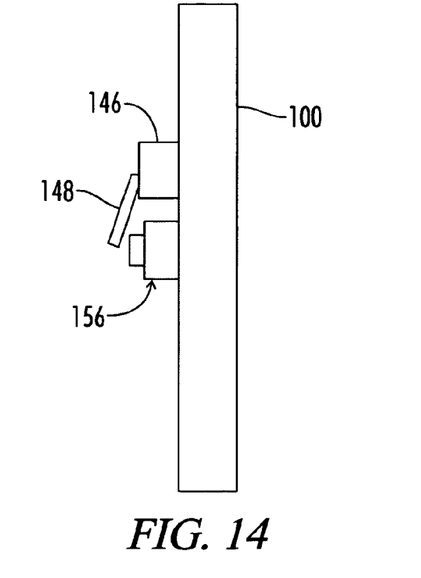
FIG. 14 is a sectional view thereof.
Figure 15:
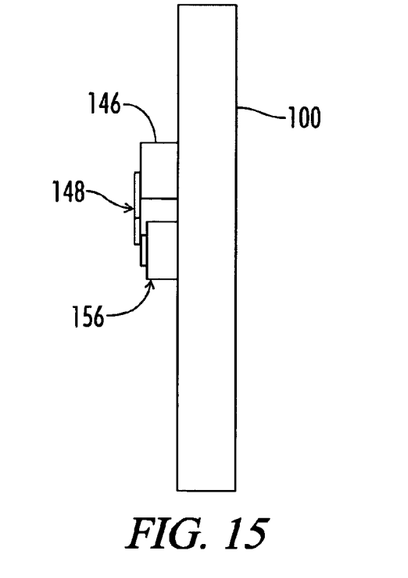
FIG. 15 is another sectional view thereof.

FIGS. 14 and 15 show the operation of access arm 148 contacting push plate 156 to open barrier 100. To contact push plate 156 to open barrier 100, a user must push access arm 148 towards push plate 156. Similar to the embodiments described above, access arm 148 has two ends, attachment end 150 and free end 152. This embodiment of the present invention also provides contact body 154 to assist the user in pivoting the access arm 148 towards the barrier 100 to contact push plate 156. A user pivots the free end 152 of access arm 148 until it contacts push plate 156 and adequately depresses the push plate 156 to open the barrier 100 as shown in FIG. 15. Cleaning substance is stored within container 146. A dispensing aperture 157 of container 146 releases the cleaning substance from the container 146 as the user opens barrier 100. The pivoting of access arm 148 causes the present invention to release the cleaning substance to the hands of the user.

Figure 16:
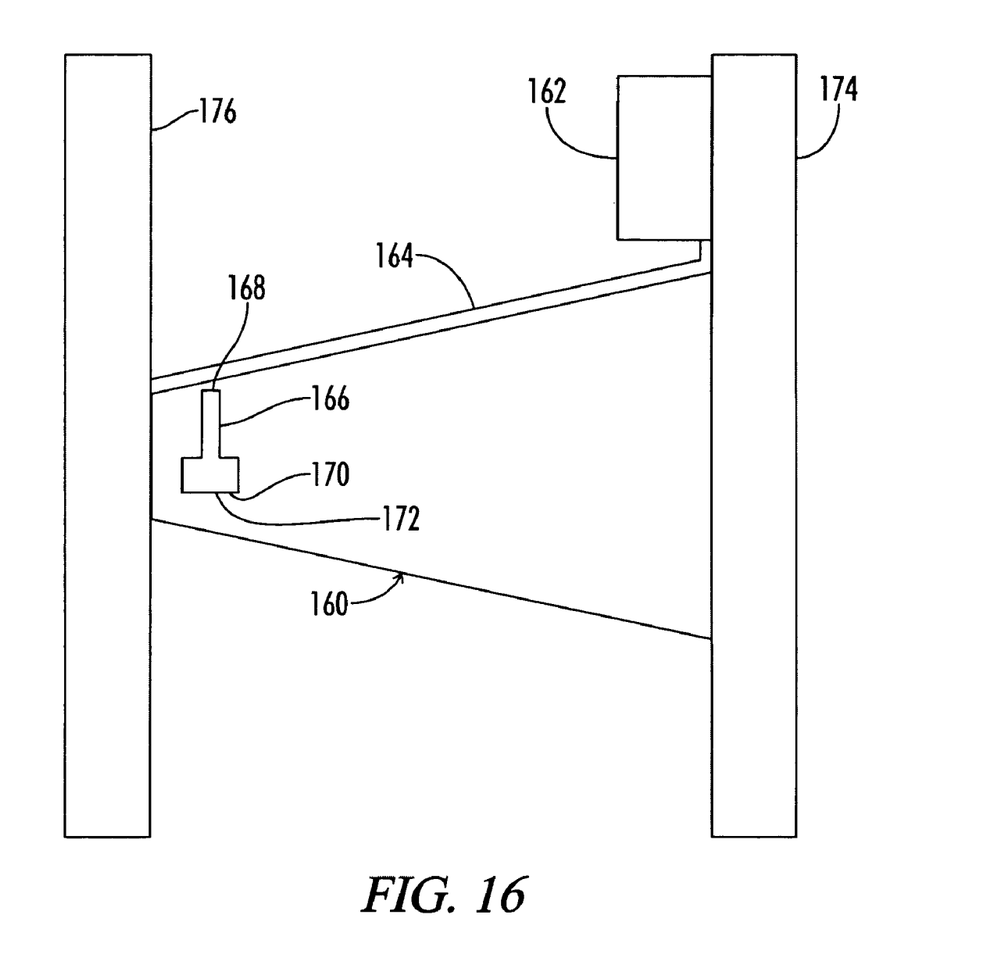
FIG. 16 is an environmental view of one embodiment of the present invention.

FIG. 16 shows another embodiment of the present invention in which a barrier 160 is installed in frame 174, 176. Container 163 holds a cleaning substance. Cleaner pathway 164 may be a hose, line, tube, pipe, or other conduit to allow cleaning substance to be released near a user's hands when opening barrier 160. Similar to previously described embodiments, the embodiment shown in FIG. 16 provides access arm 166 for opening barrier 160. Access arm 166 has two ends, attachment end 168 and free end 170. Similarly, access arm 166 provides contact body 172 for pivoting access arm 166 towards or away from barrier 160. As described above, access arm 166 can be pivoted either towards or away from barrier 160 depending on whether the barrier must be pushed or pulled to be opened. As described above, access arm adjusts a locking finger between an prevent access position and an allow access position. Similarly, locking finger is adapted to enter a receiving aperture to maintain barrier 160 in the closed position. In this embodiment, container 162 supplies both sides of barrier 164. Other embodiments of the present invention described herein can be supplied with cleaning substance from a single container.

Figure 17:
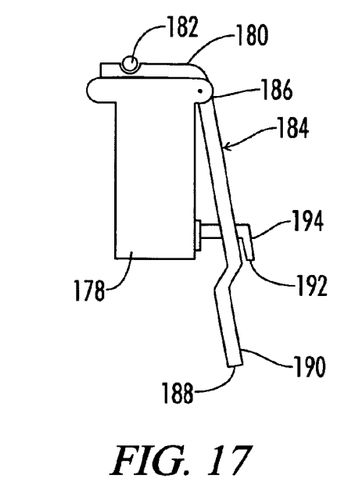
FIG. 17 is a left side view of one embodiment of the present invention.
Figure 18:
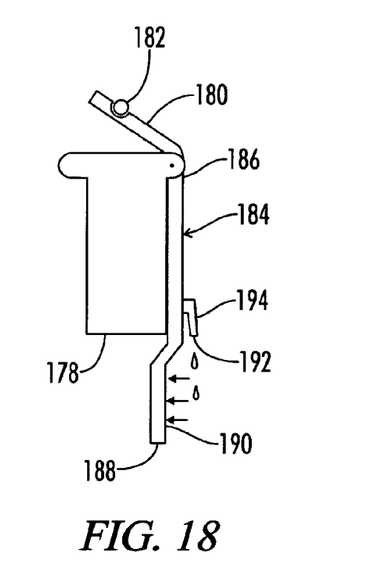
FIG. 18 is another left side view thereof.

FIGS. 17 and 18 show a different embodiment of the present invention that utilizes locking finger 182 that is guided to a receiving aperture such as a notch to prevent barrier 100 from opening. Similar to the above described embodiments, the embodiment shown in FIGS. 17 and 18 provide access arm 184 with attachment end 186 and free end 188 and container 178 storing the cleaning substance. This embodiment also provides contacting body 192 for assisting the user in pivoting access arm 184 towards or away from the barrier. This embodiment of the present invention provides access arm 184 that is connected to an adjustment arm which in this instance is lifting arm 180. Lifting arm 180 pivots according to movement of access arm 184. Lifting arm 180 raises locking finger 182 from the notch to allow the barrier to be opened. The embodiment shown in FIGS. 17 and 18 show a dispenser that releases cleaning substance as access arm 184 is pushed towards a barrier. FIG. 17 shows access arm in the lock position and lifting arm 180 in the prevent access position. FIG. 18 shows access arm 184 in the unlock position and lifting arm 180 in the allow access position. Pivoting access arm 184 to the unlock position causes this embodiment to release cleaning substance from dispensing aperture 192. This embodiment of the present invention may also include nozzle 194. Pivoting access arm 184 to the unlock position also causes lifting arm 180 to raise locking finger 182 to open the barrier.

The present invention also provides an embodiment that requires a user to pivot the access arm away from barrier prior allowing access beyond barrier. Pivoting access arm away from the barrier also releases cleaning substance. This embodiment requires a user to pivot access arm similarly as the embodiment shown in FIGS. 5 and 6. In this embodiment, pivoting the free end of access arm away from barrier to the unlock position causes lifting arm to raise locking finger 182 to open the barrier. Pivoting of the access arm to the unlock position also causes dispensing aperture to release the cleaning substance.

Figure 19:
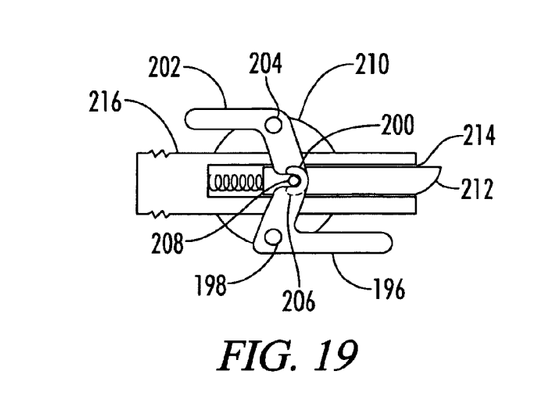
FIG. 19 is a sectional view of one embodiment of the present invention.
Figure 20:
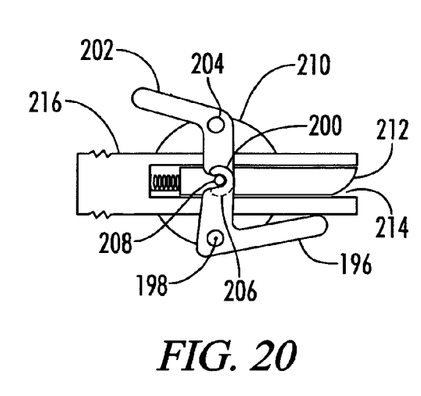
FIG. 20 is another sectional view thereof.

FIGS. 19 and 20 show another embodiment of the present invention that utilizes a different method of adjusting locking finger 212. As described above, locking finger 212 moves within locking aperture 214 of barrier 216 to open and close barrier 216. As described above, adjustment arms 196, 202 attach to an access arm that causes a cleaning substance to be released to a user as the user pivots the access arm towards or away from barrier 216. Adjustment arms 196, 202 pivotally attach to adjustment body 210 at attachment elbows 198, 204. Adjustment arms 196, 202 provide adjustment fingers 200, 206 respectively. Adjustment fingers 200, 206 contact locking bit 208. Locking bit 208 extends from locking arm 212 to allow adjustment arms 198, 204 and adjustment fingers 200, 206 to adjust locking finger 212 between the prevent access position shown in FIG. 18 and the allow access position shown in FIG. 19. Adjustment fingers 200, 206 cause locking finger 212 to withdraw into locking aperture 214 to the allow access position and extend from locking aperture 214 to the prevent access position. Adjustment fingers 200, 206 operate independently to open barrier 216. Adjustment finger 200 moves independently in relation to adjustment finger 206. Likewise, adjustment finger 206 moves independently in relation to adjustment finger 200. The independence of adjustment fingers 200, 206 allows opening of the barrier without releasing the cleaning substance on both sides of the barrier.

As adjustment arm 196 pivots toward barrier 216, adjustment finger 200 forces locking bit 208 further within locking aperture 214. The movement of locking bit 208 withdrawing into locking aperture 214 causes locking finger 212 to also withdraw into locking aperture 214. As shown in the transition from FIG. 19 to FIG. 20, adjustment arm 196 pivots towards barrier 216. Adjustment finger 200 forces locking bit 208 and locking finger 212 to withdraw into locking aperture 214 to adjust locking finger 212 from the prevent access position shown in FIG. 19 to the allow access position shown in FIG. 20.

As adjustment arm 202 pivots away from barrier 216, adjustment finger 206 forces locking bit 208 further within locking aperture 214. The movement of locking bit 208 withdrawing into locking aperture 214 causes locking finger 212 to also withdraw into locking aperture 214. As shown in the transition from FIG. 19 to FIG. 20, adjustment arm 202 pivots away from barrier 216. Adjustment finger 206 forces locking bit 208 and locking finger 212 to withdraw into locking aperture 214 to adjust locking finger 212 from the prevent access position shown in FIG. 19 to the allow access position shown in FIG. 20.

The present invention also teaches a method for mechanically preventing access to an area that requires a user to pass a barrier prior to entering an area. The present invention restricts access to the area to only those who have passed the barrier. A locking finger of the present invention in the prevent access position prevents the barrier from adjusting to an open position that allows a user to pass through the barrier. The present invention requires a user to pivot a free end of an access arm to adjust the access arm from a lock position to an unlock position. Depending upon the type of barrier, the free end of the access arm may be pivoted towards the barrier or away from the barrier to allow access. For barriers that require a user to push the barrier open, the user must pivot the free end of the access arm towards the barrier to an unlock position. For barriers that require a user to pull the barrier open, the user must pivot the free end of the access arm away from the barrier to an unlock position. Pivoting the free end of the access arm to the unlock position causes the present invention to release an amount of cleaning substance on user's hands. Pivoting the free end of the access arm to the unlock position adjusts the locking finger from the prevent access position to the allow access position. The locking finger in the allow access position allows the barrier to move to the open position to allow a user to pass through the barrier. In some embodiments, the locking finger is biased to the prevent access position to require the user to clean his hands before allowing access.

In one embodiment of the method, the access arm adjusts an adjustment arm that directly contacts the locking finger. When the access arm is pivoted, the access arm changes the position of the adjustment arm. The movement of the adjustment arm changes the position of the locking finger. The adjustment arm manipulates the locking finger to adjust the locking finger between the prevent access position and the allow access position.

From the foregoing, it will be seen that the present invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. An apparatus that dispenses a cleaning substance prior to being granted access beyond a barrier, the apparatus comprising:
   a container for storage of the cleaning substance;
   a dispensing aperture adapted to release the cleaning substance from said container;
   a locking finger adapted to adjust between an allow access position and a prevent access position, said locking finger in said allow access position allowing a user to open the barrier when the barrier is in a closed position, said locking finger in said prevent access position not allowing a user to adjust the barrier from a closed position to an open position; and
   an access arm adapted to pivot in relation to said barrier, said access arm adapted to pivot towards the barrier and away from the barrier, said access arm adapted to pivot between a lock position and an unlock position, said access arm in said lock position places said locking finger in said prevent access position, said access arm in said unlock position places said locking finger in said access position.

2. The apparatus of claim 1 wherein said access arm further comprises a contact body, said contact body adapted to be contacted by user to adjust said access arm from said lock position to said unlock position.

3. The apparatus of claim 1 wherein said access arm has an attached end and a free end, said attached end of the access arm hingeably attaches to said container, said free end of said access arm pivots around said attached end.

4. The apparatus of claim 3 wherein said free end of said access arm pivots toward said barrier to adjust said access arm to said unlock position to place said locking finger to said allow access position.

5. The apparatus of claim 3 wherein said free end of said access arm pivots away from said barrier to adjust said access arm to said unlock position to place said locking finger to said allow access position.

6. The apparatus of claim 1 wherein said access arm has an attached end and a free end, said attached end of the access arm hingeably attaches to said barrier, said free end of said access arm pivots around said attached end.

7. The apparatus of claim 3 wherein said free end of said access arm pivots toward said barrier to adjust said access arm to said unlock position to place said locking finger to said allow access position.

8. The apparatus of claim 3 wherein said free end of said access arm pivots away from said barrier to adjust said access arm to said unlock position to place said locking finger to said allow access position.

9. The apparatus of claim 1 further comprising:
an adjustment aperture in said locking arm; and
an adjustment arm attached to said access arm, said adjustment arm adapted to move within said adjustment aperture, wherein movement of said adjustment arm within said adjustment aperture adjusts the locking finger between the prevent access position and the allow access position.

10. The apparatus of claim 1 further comprising:
a receiving aperture adjacent to the barrier;
wherein said adjustment arm is a lifting arm, said lifting arm adapted to raise said locking finger from said receiving aperture to the allow access position, said lifting arm adapted to lower said locking finger into said receiving aperture to the prevent access position.

11. The apparatus of claim 1 wherein said dispensing aperture releases the cleaning substance towards said access arm.

12. The apparatus of claim 1 wherein said locking finger is adapted to enter a receiving aperture adjacent to the barrier.

13. An apparatus that dispenses a cleaning substance prior to being granted access beyond a barrier, the apparatus comprising:
a container for storage of the cleaning substance;
a locking finger adapted to adjust between an allow access position and a prevent access position, said locking finger in said allow access position allowing a user to open the barrier when the barrier is in a closed position, said locking finger in said prevent access position not allowing a user to adjust the barrier from a closed position to an open position;
an access arm adapted to pivot in relation to said barrier, said access arm adapted to pivot towards the barrier and away from the barrier, said access arm adapted to pivot between a lock position and an unlock position, said access arm in said lock position places said locking finger in said prevent access position, said access arm in said unlock position places said locking finger in said access position, said access arm biased to said lock position; and
a dispensing aperture in said container, said dispensing aperture adapted to release said the cleaning substance from said container when said access arm is in said unlock position.

14. The apparatus of claim 13 wherein said access arm has an attached end and a free end, said attached end of the access arm fixed in relation to said barrier, said free end of said access arm pivots around said attached end, said free end of said access arm pivots toward said barrier to adjust said access arm to said unlock position to place said locking finger to said allow access position.

15. The apparatus of claim 13 wherein said access arm has an attached end and a free end, said attached end of the access arm fixed in relation to said barrier, said free end of said access arm pivots around said attached end, said free end of said access arm pivots away from said barrier to adjust said access arm to said unlock position to place said locking finger to said allow access position.

16. The apparatus of claim 13 further comprising:
an adjustment aperture in said locking arm;
an adjustment arm attached to said access arm; and
an adjustment finger of said access arm, said adjustment finger adapted to move within said adjustment aperture, said adjustment finger shaped to adjust said locking finger between said prevent access position and said allow access position, said movement of said adjustment finger within said adjustment aperture adjusts the locking finger between the prevent access position and the allow access position.

17. The apparatus of claim 13 further comprising:
a locking bit fixedly attached to said locking arm;
an adjustment arm attached to said access arm, said adjustment arm pivotally attached to an adjustment body, said adjustment arm adapted to pivot as said access arm pivots between said lock position and said unlock position;
an adjustment finger of said adjustment arm, said adjustment finger adapted to receive and release said locking bit of said locking arm, said adjustment finger adapted to move said locking bit to adjust said locking finger between said prevent access position and said allow access position as said adjustment arm pivots.

18. The apparatus of claim 13 further comprising:
a push plate of said barrier;
said access arm adapted to contact said push plate to adjust said barrier to said open position; and
at least one guarding body, said guarding body adapted to prevent a user from contacting at least at least a portion of said push plate, said guarding body adapted to allow said access arm to contact said push plate.

19. A method of maintaining a sterile environment, the method comprising:
preventing access to an area with a barrier;
providing a container storing cleaning substance;
requiring a user to pivot a free end of said an access arm to adjust said access arm from a lock position to an unlock position;
dispensing said cleaning substance from said container;
adjusting a locking finger from a prevent access position that maintains the barrier in a closed position to an allow access position that allows the barrier to open, adjusting said locking from the prevent access position to the allow access position when said access arm is placed in the unlock position.

20. The method of claim 19 wherein the step of requiring a user to pivot a free end of said access arm further comprises:
pivoting said free end of said access toward or away from said barrier to place said access arm in said unlock position.

* * * * *